US009920005B2

United States Patent
Komatsu et al.

(10) Patent No.: US 9,920,005 B2
(45) Date of Patent: *Mar. 20, 2018

(54) METHOD FOR CRYSTALLIZATION OF 2-AMINO-2-[2-[4-(3-BENZYLOXYPHENYL-THIO)-2-CHLOROPHENYL]ETHYL]-1,3-PROPANEDIOL HYDROCHLORIDE

(71) Applicant: Kyorin Pharmaceutical Co., Ltd., Chiyoda-ku (JP)

(72) Inventors: Hidetaka Komatsu, Shimotsuga-gun (JP); Hiroya Satoh, Shimotsuga-gun (JP)

(73) Assignee: KYORIN PHARMACEUTICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/281,942

(22) Filed: Sep. 30, 2016

(65) Prior Publication Data
US 2017/0015624 A1   Jan. 19, 2017

Related U.S. Application Data

(63) Continuation of application No. 12/934,577, filed as application No. PCT/JP2009/055235 on Mar. 18, 2009.

(30) Foreign Application Priority Data

Mar. 24, 2008   (JP) .................. 2008-076124

(51) Int. Cl.
*A61K 31/138*   (2006.01)
*C07C 319/28*   (2006.01)
*C07C 213/10*   (2006.01)

(52) U.S. Cl.
CPC ........ *C07C 319/28* (2013.01); *C07B 2200/13* (2013.01)

(58) Field of Classification Search
None
See application file for complete search history.

(56) References Cited

U.S. PATENT DOCUMENTS 5,475,138 A   12/1995   Pal et al.
6,960,692 B2  11/2005   Kohno et al.
(Continued)

FOREIGN PATENT DOCUMENTS

CN   1561331 A    1/2005
CN   101072752 A  11/2007
(Continued)

OTHER PUBLICATIONS

Hamada, Maiko et al., "Efficient Synthesis of the Immunomodulating Compound KRP-203", Synthesis, No. 13, pp. 1927-1929, (2007).

(Continued)

*Primary Examiner* — Marcos L Sznaidman
*Assistant Examiner* — Rayna Rodriguez
(74) *Attorney, Agent, or Firm* — Oblon, McClelland, Maier & Neustadt, L.L.P.

(57) ABSTRACT

A method for highly efficiently preparing high purity crystals of 2-amino-2-[2-[4-(3-benzyloxyphenylthio)-2-chlorophenyl]-ethyl]-1,3-propanediol hydrochloride. The method involves dissolving 2-amino-2-[2-[4-(3-benzyloxyphenylthio)-2-chlorophenyl]ethyl]-1,3-propanediol in a mixed solvent comprising a solvent in which its hydrochloride is highly soluble and a solvent in which its hydrochloride is less soluble, to prepare a solution of 2-amino-2-[2-[4-(3-benzyloxyphenylthio)-2-chlorophenyl]ethyl]-1,3-propanediol; and then adding hydrochloric acid to the resulting solution with stirring, to crystallize the hydrochloride of 2-amino-2-[2-[4-(3-benzyloxyphenylthio)-2-chloro-phenyl]ethyl]-1,3-propanediol.

16 Claims, 1 Drawing Sheet

(56) References Cited

U.S. PATENT DOCUMENTS

| | | |
|---|---|---|
| 7,456,157 B2 | 11/2008 | Kohno et al. |
| 7,482,491 B2 | 1/2009 | Kohno et al. |
| 7,759,326 B2 | 7/2010 | Kohno et al. |
| 7,763,752 B2 | 7/2010 | Kohno et al. |
| 7,795,472 B2 | 9/2010 | Tsubuki et al. |
| 2004/0254222 A1 | 12/2004 | Kohno et al. |
| 2008/0207941 A1 | 8/2008 | Tsubuki et al. |
| 2009/0082311 A1 | 3/2009 | Kiuchi et al. |

FOREIGN PATENT DOCUMENTS

| | | |
|---|---|---|
| EP | 1 806 338 A1 | 7/2007 |
| EP | 2 017 257 A1 | 1/2009 |
| KR | 10-2007-0073895 | 7/2007 |
| RU | 2007 117 372 A | 11/2008 |
| WO | WO 2003/029205 | 4/2003 |
| WO | WO 2003/029205 A1 | 4/2003 |
| WO | WO 2004/026817 A1 | 4/2004 |
| WO | WO 2004/074297 A1 | 9/2004 |
| WO | WO 2006/041019 | 4/2006 |
| WO | WO 2006/041019 A1 | 4/2006 |
| WO | WO 2007/126042 | 11/2007 |

OTHER PUBLICATIONS

Chino, Masao et al., "An Efficient Total Synthesis of a Sphingosine-1-Phosphate Receptor Agonist KRP-203", Tetrahedron, vol. 64, pp. 3859-3866, (2008).

Biswajit Kalita, et al., "Synthesis of 2-Nitroalcohols by Regioselective Ring Opening of Epoxides with $MgSO_4$/MeOH/$NaNO_2$ System: A Short Synthesis of Immunosuppressive Agent FTY-720", Synlett 2001, No. 9, 2001, pp. 1411-1414.

Nathan Kornblum, et al., "A New Method for the Synthesis of Aliphatic Nitro Compounds", J. Am. Chem. Soc., vol. 78, 1956, pp. 1497-1501 (with an additional page).

Combined Office Action and Search Report dated Nov. 5, 2012 in Chinese Patent Application No. 200980119026.5 with English translation of categories of cited documents.

Decision of Patent Grant dated Dec. 5, 2012 in Russian Patent Application No. 2010143432/04 (with English-language translation).

Office Action dated Sep. 16, 2013 issued in corresponding Chinese Application No. 200980119026.5, filed Mar. 18, 2009 (without English translation).

Chau-Chyun Chen et al., "Correlation and Prediction of Drug Molecule Solubility in Mixed Solvent Systems with the Nonrandom Two-Liquid Segment Activity Coefficient (NRTL-SAC) Model", Ind. Eng. Chem. Res., vol. 45, No. 13, May 26, 2006, pp. 4816-4824.

Extended European Search Report issued in corresponding European Application No. 09724232.5 filed Mar. 18, 2009.

Office Action dated Jun. 12, 2015, in Korean Patent Application No. 1020107023600, filed Oct. 22, 2010.

Chen C and Crafts PA. "Correlation and Prediction of Drug Molecule Solubility in Mixed Solvent Systems with the Nonrandom Two-Liquid Segment Activity Coefficient (NRTL-SAC) Model." Ind. Eng. Chem. Res. 2006; 45:4816-4824.

Sigma Aldrich Ethanol MSDS.

Sigma Aldrich Ethyl Acetate Chemical Information.

Takeshi et al.; WO 2006/041019 A1; 2006 MT provided by Espacenet on Aug. 16, 2012.

METHOD FOR CRYSTALLIZATION OF 2-AMINO-2-[2-[4-(3-BENZYLOXYPHENYLTHIO)-2-CHLOROPHENYL]ETHYL]-1,3-PROPANEDIOL HYDROCHLORIDE

CROSS REFERENCE TO RELATED APPLICATIONS

The present application is a continuation of and claims the benefit of priority to U.S. application Ser. No. 12/934,577, filed Sep. 24, 2010, which is a National Stage of PCT/JP2009/055235, filed Mar. 18, 2009, which further claims the benefit of priority to Japanese Patent Application No. 2008-076124, filed Mar. 24, 2008. The entire contents of these applications are incorporated herein by reference.

BACKGROUND ART

Hydrochloride of 2-amino-2-[2-[4-(3-benzyloxyphenylthio)-2-chlorophenyl]-ethyl]-1,3-propanediol (hereunder referred to as the "compound of the present invention") is a compound having a substituted diaryl sulfide structure and having an excellent immunosuppressive action and there has been reported that the compound of the present invention is effective for the treatment of the autoimmune diseases such as chronic rheumatoid arthritis (see Patent Document 1).

Patent Document 1 discloses a method for the crystallization of the compound of the present invention which comprises the step of crystallizing the compound through the addition of an ethyl acetate solution of hydrochloric acid to a methanol solution of the compound (see Example 36). In addition, Patent Document 2 discloses a method for the crystallization of the compound of the present invention, which comprises the steps of adding a 6 mole/L of hydrochloric acid to a solution of the compound of the present invention in ethyl alcohol and then adding ethyl acetate to the resulting solution (see Example 4). These methods are ones in which hydrochloric acid is dissolved in ethyl acetate and then the resulting hydrochloric acid solution is added to a solution of the compound of the present invention in an alcohol; or hydrochloric acid is added to an alcoholic solution of the compound of the present invention and then ethyl acetate is added to the resulting mixture.

Patent Document 1: WO 03/029205, Pamphlet;
Patent Document 2: WO 06/041019, Pamphlet.

DISCLOSURE OF THE INVENTION

Problems that the Invention is to Solve

The crystallization methods disclosed in these conventional techniques suffer from such a disadvantage that fiber-like crystals are immediately precipitated out of the solution simultaneous with the addition of hydrochloric acid and that the fiber-like crystals quickly and densely undergo agglomeration and they are thus converted into large crystalline grains or masses. In this respect, the fiber-like crystals are extremely dense to such an extent that the crystallization system cannot be stirred at all even when one intends to stir the system. For this reason, various problems arise such that the resulting crystals can be removed from the crystallization device with great difficulty and that the filtration efficiency of the crystals is accordingly reduced. Moreover, the crystals are agglomerated to such an extent that the resulting agglomerated crystalline masses are free of any vacant space and therefore, this in turn results in further disadvantages such that impurities such as the solvent used are trapped within the crystals and that the remaining impurities would surely reduce the purity of the resulting crystalline product. In this connection, it is a matter of course that the crystalline masses can be converted into fine crystalline grains through the pulverization of the masses. However, this method would suffer from additional problems such that it requires an additional step for pulverizing the crystalline masses, that this may accordingly require extra steps accompanied by the pulverization step and that the crystal-production efficiency is greatly reduced in the preparation of a crystalline product for the market.

Accordingly, it is the present invention to provide a method for the production of crystals, which permits the production of crystals, of a compound, in the form of crystalline particles having a small and relatively uniform particle size through the crystallization and which permits, as a result, the highly efficient production of the crystals thereof having a low content of impurities.

Means for the Solution of the Problems

The inventors of this invention have conducted intensive studies to solve the foregoing problems, have found that the compound of the present invention can unexpectedly be crystallized without being accompanied by the solidification of the hydrochloride of the compound upon the crystallization if the order of the addition of hydrochloric acid is changed, and have thus completed the present invention.

Accordingly, the present invention relates to a method for the crystallization of 2-amino-2-[2-[4-(3-benzyloxyphenylthio)-2-chlorophenyl]ethyl]-1,3-propanediol hydrochloride, which comprises the following steps:

(1) dissolving 2-amino-2-[2-[4-(3-benzyloxyphenylthio)-2-chlorophenyl]ethyl]-1,3-propanediol in a mixed solvent comprising a solvent in which the compound in the form of the hydrochloride thereof is highly soluble and a solvent in which the hydrochloride is less soluble to thus prepare a solution of 2-amino-2-[2-[4-(3-benzyloxyphenylthio)-2-chlorophenyl]ethyl]-1,3-propanediol; and then
(2) adding hydrochloric acid to the foregoing solution with stirring to thus crystallize the hydrochloride of 2-amino-2-[2-[4-(3-benzyloxyphenylthio)-2-chloro-phenyl]ethyl]-1,3-propanediol.

BEST MODE FOR CARRYING OUT THE INVENTION

The present invention will now be described in more detail below.

The compound of the present invention is 2-amino-2-[2-[4-(3-benzyloxyphenylthio)-2-chlorophenyl]-ethyl]-1,3-propanediol represented by the following chemical formula. This compound has already been known and the compound shows an excellent immunosuppressive effect and has been recognized to be effective for the treatment of autoimmune diseases such as chronic rheumatoid arthritis.

[Chemical Formula 1]

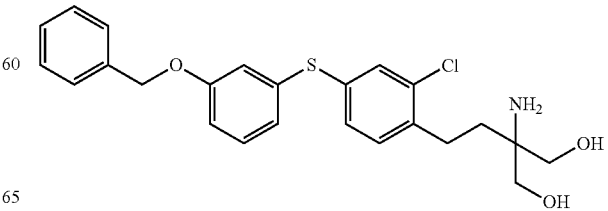

In the method of the present invention, the compound of the present invention is first dissolved in a mixed solvent. The mixed solvent comprises a solvent in which the compound of the present invention in the form of the hydrochloride thereof is highly soluble (a good solvent) and a solvent in which the compound in its hydrochloride is less soluble (a poor solvent). The good solvent comprises a hydrophilic organic solvent and specific examples thereof suitably used herein include methanol, ethanol, propyl alcohol, isopropyl alcohol, butanol, t-butanol, acetonitrile and propionitrile. On the other hand, examples of the poor solvents suitably used herein are water, ethyl formate, ethyl acetate, propyl acetate, ethyl propionate, diethyl ether, diisopropyl ether, and ethylene glycol dimethyl ether.

It is suitable that the amount of the mixed solvent to be used is, for instance, not less than 20 times the mass of the compound of the present invention and preferably 20 to 50 times the mass thereof.

In the mixed solvent, particularly suitably used therein are, for instance, ethanol and isopropyl alcohol as the good solvent; and ethyl acetate, water and isopropyl ether as the poor solvent.

For instance, it is suitable that the mixing ratio of the good solvent to the poor solvent (the good solvent/the poor solvent ratio, by mass) ranges, for instance, from 1/4 to 1/1 and preferably 1/2 to 2/3. For instance, in case of a methanol/ethyl acetate ranges, for instance, from 1/4 to 1/1 and preferably 1/2 to 2/3. For instance, the ratio is particularly preferably 2/3.

In the step (1) of the method according to the present invention, the compound of the present invention is dissolved in a good solvent with heating, then a poor solvent is added to the resulting solution, followed by the initiation of the stirring of the mixture.

The compound of the present invention is suitably dissolved in the mixed solvent at a temperature ranging from 50 to 90° C. and preferably 60 to 70° C.

When dissolving the compound of the present invention in such a mixed solvent, it is preferred to stir the mixed solvent using a rotor (or a stirrer) or a rotating blade. In this respect, however, the means for stirring the mixed solvent usable herein may be a method for stirring the same through shaking and a stirring method through the application of ultrasonics. When stirring the mixed solvent using a stirrer or a rotating blade, the stirring rate may be any one inasmuch as it can be used in the usual crystallization process, but it is preferably not less than 50 m/min and more preferably not less than 100 m/min as expressed in terms of the tip speed. The use of such a high speed stirring operation would permit the formation of finer particulate crystals.

In the step (2), hydrochloric acid is added to the solution of the compound of the present invention in a mixed solvent with heating and under stirring. Thus, the compound of the present invention in the form of the hydrochloride thereof initiates crystallization.

The temperature required for the foregoing heating operation may arbitrarily be set at a level suitable for maintaining the hydrochloride of the compound of the present invention in its dissolved condition, but it is preferred to set the temperature at a level preferably ranging from 50 to 90° C. and more preferably 60 to 70° C. The stirring operation may be the same as that discussed above in connection with the step (1). In particular, if the temperature is reduced to a level of not more than about 60° C., the compound of the present invention is actively converted into its crystals.

In addition, the concentration of hydrochloric acid used herein may be any one inasmuch as it can be sufficient for converting the compound of the present invention into its the hydrochloride, but it is suitable that the concentration thereof preferably ranges from 1 to 12 mole/L and it further preferably ranges from 3 to 6 mole/L.

In addition, the method of the present invention suitably comprises, as the step (3), a step for cooling, with stirring, the solution prepared in the step (2). The cooling temperature may arbitrarily be set at a level sufficient for actively precipitating the hydrochloride of the compound of the present invention. It is suitable that the cooling temperature ranges, for instance, from 0 to 30° C. and preferably 5 to 25° C.

The crystals thus prepared are filtered off from the crystallization system, then washed and finally dried.

The conditions for the stirring operation in the foregoing optional step (3) and the cooling temperature used therein are the same as those described above in connection with the step (2).

In the foregoing washing step, any appropriate solvent may arbitrarily be selected and used therein, but preferably used herein is a mixed solvent comprising a good solvent and a poor solvent and one specific example thereof preferably used in the present invention is a mixed solvent comprising ethyl acetate and ethanol.

The compound: 2-amino-2-[2-[4-(3-benzyloxyphenylthio)-2-chlorophenyl]ethyl]-1,3-propanediol used in the present invention can be prepared according to the method disclosed in Patent Document 1 or 2.

Moreover, the resulting crystals of 2-amino-2-[2-[4-(3-benzyloxyphenylthio)-2-chlorophenyl]ethyl]-1,3-propanediol hydrochloride may be formulated into a pharmaceutical preparation by the addition, to the crystals, of any excipient disclosed in WO 2007/043433 according to the method likewise disclosed therein.

EXAMPLES

The present invention will now be described in more detail with reference to the following Examples or the like, but the present invention is not restricted to these specific Examples or the like, at all.

Example 1

There was dissolved, in ethanol (purity: 99.5%; 42.0 mL), 6.00 g of 2-amino-2-[2-[4-(3-benzyloxyphenylthio)-2-chlorophenyl]ethyl]-1,3-propanediol with heating (dissolution temperature: 43° C.), and then 108 mL of ethyl acetate was added to the resulting solution.

A 6 mole/L hydrochloric acid (2.48 mL) was introduced into the foregoing solution at an inner temperature ranging from 60 to 70° C., while stirring, with heating, the solution at a tip speed of 157 m/min (stirring blade: 10 cm; number of rotations: 500 rpm). After confirming the precipitation of crystals (crystal-deposition temperature: 63° C.), the crystallization system was stirred at an inner temperature ranging from 60 to 70° C. for 10 minutes. Then, the crystallization system was cooled and stirred at an inner temperature of not higher than 25° C. for 30 minutes. After filtering off of the precipitated crystals, the crystals recovered through the filtration were washed with 36.0 mL of a preliminarily prepared ethanol (99.5%)/ethyl acetate mixed solvent (mixing ratio: 1:1) and the liquid was subsequently removed. The resulting crystals were dried under reduced pressure at a predetermined temperature of 60° C. to thus give 5.49 g (yield: 84.6%) of the hydrochloride of the compound of the present invention.

In Example 1, the crystals were separated from the crystallization system during the stirring operation in the form of fine particles as compared with those prepared according to Comparative Example 1 as will be detailed below. FIG. 1 is an electron micrograph showing the fine structure of the crystals prepared in an experiment according to Example 1 and FIG. 2 is a photograph showing the precipitated state of the crystals obtained through the crystallization in an experiment according to Example 1. Thus, according to Example 1 of the present invention, fine crystals having vacant spaces within the same can be obtained by dissolving the compound of the present invention in a mixed solvent comprising a good solvent and a poor solvent and finally adding hydrochloric acid and the compound of the present invention (in the form of its hydrochloride) is crystallized in the form of finer particles. Accordingly, unlike the conventional techniques, the present invention never requires the use of any pulverization treatment to obtain a desired product in a high efficiency. Moreover, the resulting crystals have a high purity since they are obtained in the form of fine particles.

Comparative Example 1 (Method Disclosed in Patent Document 2)

To 95.0 mL of ethanol, there was added 19.0 g (42.8 mmol) of 2-amino-2-[2-[4-(3-benzyloxyphenylthio)-2-chlorophenyl]ethyl]-1,3-propanediol and then the resulting mixture was stirred with heating at an external temperature ranging from 50 to 60° C. to thus dissolve the compound in the solvent. The solution was filtered off while it was still hot and the precipitate was washed with 38.0 mL of ethanol. The resulting filtrate was stirred with heating and there was added, to the filtrate in a stroke, a mixed solvent comprising 3.92 mL (47.1 mmol) of hydrochloric acid and 3.92 mL of purified water at an inner temperature of 60 to 70° C. After the precipitation of crystals, the crystallization system was stirred for 5 minutes, then 266 mL of ethyl acetate was added thereto and the mixture was then stirred at an inner temperature ranging from 50 to 60° C. for 10 minutes. The system was cooled with stirring and further stirred at an inner temperature of not higher than 25° C. for 30 minutes. The crystals thus precipitated were filtered off and washed with a mixed liquid comprising 28.5 mL of ethanol and 28.5 mL of ethyl acetate. The resulting crystals were dried while blowing the air in through the same for 30 minutes (wet crystals were crushed or triturated prior to the drying step through air-blowing) and the drying through air-blowing was then continued at 60° C. for 20 hours to thus obtain white powder and white masses. The resulting product was pulverized using a mortar and a pestle to thus give 19.3 g (40.1 mmol, yield: 94%) of 2-amino-2-[2-[4-(3-benzyloxy-phenylthio)-2-chlorophenyl]ethyl]-1,3-propanediol hydrochloride as white powdery crystals.

In Comparative Example 1, hydrochloric acid is not added after the compound of the present invention is dissolved in a mixed solvent comprising a good solvent and a poor solvent, but hydrochloric acid is added after the compound of the present invention is dissolved in ethanol as a good solvent and then ethyl acetate as a poor solvent is added to the resulting mixture. For this reason, the hydrochloride of the compound rapidly undergoes crystallization and the crystals thereof are thus obtained in the form of dense masses. FIG. 3 is an electron micrograph showing the fine structure of the crystals prepared in an experiment according to Comparative Example 1 and FIG. 4 is a photograph showing the crystalline forms of the crystals obtained through the crystallization in an experiment according to Comparative Example 1. The data as shown in FIG. 3 clearly indicate that the crystallization method disclosed in Comparative Example 1 provides fibrous crystals which are free of any vacant space within the same and which are in a densely agglomerated state. In addition, the crystals obtained in Comparative Example 1 are in a unified mass as will be seen from FIG. 4.

According to the crystallization method of Comparative Example 1, various problems thus arise such that the crystals obtained can be removed from the crystallization reactor, with great difficulty, that when preparing a crystalline product for the market, the method further requires the use of a pulverization step and that impurities such as the solvents used still remain within the crystals. Accordingly, the method is inefficient and cannot provide a product having a high purity.

INDUSTRIAL APPLICABILITY

As has been discussed above in detail, the present invention thus permits the effective production of highly pure and fine crystals of 2-amino-2-[2-[4-(3-benzyloxy-phenylthio)-2-chlorophenyl]-ethyl]-1,3-propanediol hydrochloride.

Figure 1:
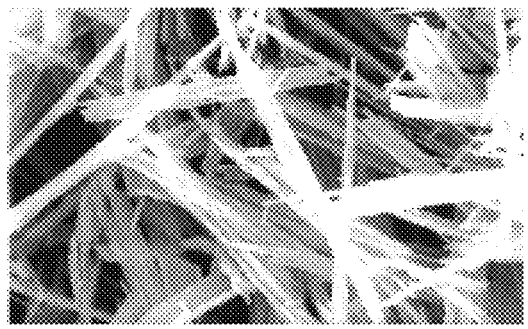
FIG. 1 is an electron micrograph showing the fine structure of the crystals obtained in an experiment according to Example 1.
Figure 2:
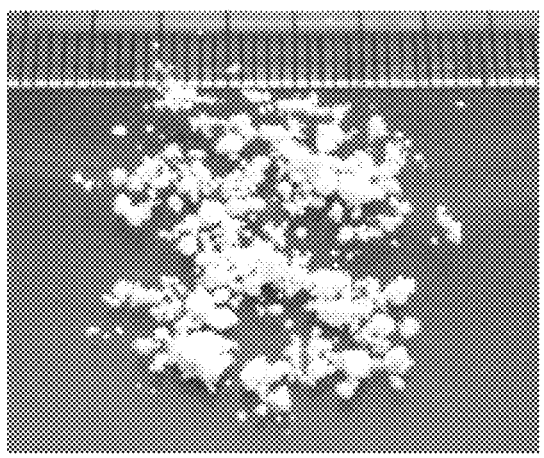
FIG. 2 is a photograph showing the condition of the crystals obtained in an experiment according to Example 1.
Figure 3:
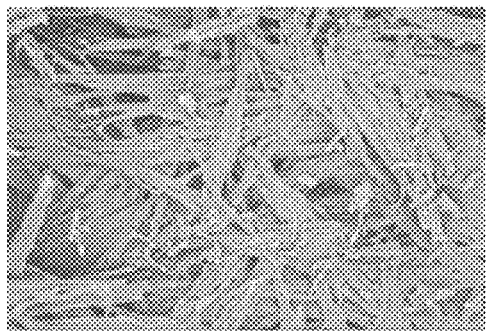
FIG. 3 is an electron micrograph showing the fine structure of the crystals obtained in an experiment according to Comparative Example 1.
Figure 4:
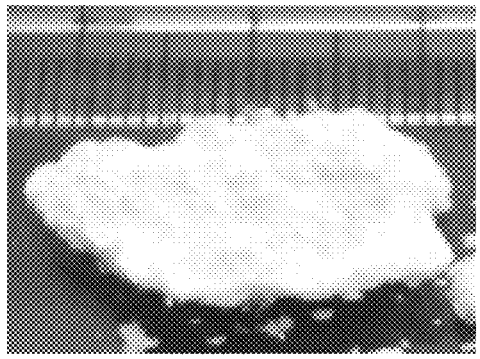
FIG. 4 is a photograph showing the condition of the crystals obtained in an experiment according to Comparative Example 1.

What is claimed is:

1. A method for crystallizing 2-amino-2-[2-[4-(3-benzyloxyphenylthio)-2-chlorophenyl]-ethyl]-1,3-propanediol hydrochloride, comprising:
   dissolving 2-amino-2-[2-[4-(3-benzyloxyphenylthio)-2-chlorophenyl]-ethyl]-1,3-propanediol in ethanol with heating;
   adding ethyl acetate to the ethanol containing the 2-amino-2-[2-[4-(3-benzyloxyphenylthio)-2-chlorophenyl]-ethyl]-1,3-propanediol, resulting in a first solution;
   adding 1 to 12 mole/L of hydrochloric acid to the first solution at a temperature in a range of 50° C. to 90° C. while stirring, resulting a second solution; and
   forming crystalline particles of 2-amino-2-[2-[4-(3-benzyloxyphenylthio)-2-chlorophenyl]-ethyl]-1,3-propanediol hydrochloride from the second solution at a temperature in a range of from 0° C. to 30° C. while stirring,
   wherein an amount of a mixed solvent comprising the ethanol and the ethyl acetate ranges from 20 to 50 times a mass of the 2-amino-2-[2-[4-(3-benzyloxyphenylthio)-2-chlorophenyl]-ethyl]-1,3-propanediol.

2. The method of claim 1, wherein the forming of the crystalline particles is carried out while stirring the second solution at a tip speed of not less than 50 m/min.

3. The method of claim 1, wherein the adding of the hydrochloric acid is carried out at a temperature in a range of from 60° C. to 70° C.

4. The method of claim 1, wherein the hydrochloric acid has a concentration ranging from 3 to 6 mole/L.

5. The method of claim 1, wherein the forming of the crystalline particles is carried out while stirring the second solution at a temperature in a range of from 5° C. to 25° C.

6. The method of claim 2, wherein the adding of the hydrochloric acid is carried out at a temperature in a range of from 60° C. to 70° C.

7. The method of claim 2, wherein the hydrochloric acid has a concentration ranging from 3 to 6 mole/L.

8. The method of claim 2, wherein the forming of the crystalline particles is carried out while stirring the second solution at a temperature in a range of from 5° C. to 25° C.

9. The method of claim 3, wherein the hydrochloric acid has a concentration ranging from 3 to 6 mole/L.

10. The method of claim 3, wherein the forming of the crystalline particles is carried out while stirring the second solution at a temperature in a range of from 5° C. to 25° C.

11. The method of claim 4, wherein the forming of the crystalline particles is carried out while stirring the second solution at a temperature in a range of from 5° C. to 25° C.

12. The method of claim 6, wherein the hydrochloric acid has a concentration ranging from 3 to 6 mole/L.

13. The method of claim 6, wherein the forming of the crystalline particles is carried out while stirring the second solution at a temperature in a range of from 5° C. to 25° C.

14. The method of claim 7, wherein the forming of the crystalline particles is carried out while stirring the second solution at a temperature in a range of from 5° C. to 25° C.

15. The method of claim 9, wherein the forming of the crystalline particles is carried out while stirring the second solution at a temperature in a range of from 5° C. to 25° C.

16. The method of claim 12, wherein the forming of the crystalline particles is carried out while stirring the second solution at a temperature in a range of from 5° C. to 25° C.

* * * * *

UNITED STATES PATENT AND TRADEMARK OFFICE
CERTIFICATE OF CORRECTION

PATENT NO. : 9,920,005 B2
APPLICATION NO. : 15/281942
DATED : March 20, 2018
INVENTOR(S) : Hidetaka Komatsu et al.

It is certified that error appears in the above-identified patent and that said Letters Patent is hereby corrected as shown below:

On the Title Page

Item (54), the Title of the Invention is incorrect. Item (54) should read:
--(54)  METHOD FOR CRYSTALLIZATION OF 2-AMINO-2-[2-[4-(3-BENZYLOXYPHENYLTHIO)-2-CHLOROPHENYL]-ETHYL]-1,3-PROPANEDIOL HYDROCHLORIDE--

Signed and Sealed this
Sixteenth Day of April, 2019

Andrei Iancu
*Director of the United States Patent and Trademark Office*